United States Patent [19]
Lewandowski et al.

[11] Patent Number: 4,897,162
[45] Date of Patent: Jan. 30, 1990

[54] PULSE VOLTAMMETRY

[75] Inventors: Jan Lewandowski, South Euclid; Paul S. Malchesky, Painesville; Yukihiko Nose', Cleveland, all of Ohio

[73] Assignee: The Cleveland Clinic Foundation, Cleveland, Ohio

[21] Appl. No.: 151,622

[22] Filed: Feb. 2, 1988

Related U.S. Application Data

[63] Continuation-in-part of Ser. No. 930,872, Nov. 14, 1986, abandoned, which is a continuation-in-part of Ser. No. 815,402, Dec. 31, 1985, abandoned.

[51] Int. Cl.$^4$ ............................................. G01N 27/50
[52] U.S. Cl. ................................... 204/1 T; 204/402; 204/403; 204/406; 204/412; 204/415
[58] Field of Search ............... 204/1 T, 1 E, 402, 403, 204/406, 415, 412

[56] References Cited

U.S. PATENT DOCUMENTS

| | | | |
|---|---|---|---|
| 3,937,615 | 2/1976 | Clack et al. | 23/253 R |
| 4,077,861 | 3/1978 | Lauer et al. | 204/195 P |
| 4,260,680 | 4/1981 | Muramatsu et al. | 435/14 |
| 4,297,184 | 10/1981 | Dyer | 204/129.4 |
| 4,340,458 | 7/1982 | Lerner et al. | 204/195 R |
| 4,366,033 | 12/1982 | Richter et al. | 204/1 T |
| 4,381,775 | 5/1983 | Nose' et al. | 604/6 |
| 4,396,464 | 8/1983 | Giner et al. | 204/1 T |
| 4,402,940 | 9/1983 | Nose' et al. | 424/101 |
| 4,403,984 | 9/1983 | Ash et al. | 604/50 |
| 4,477,314 | 10/1984 | Richter et al. | 204/1 T |
| 4,561,944 | 12/1985 | Sasaki et al. | 204/33 |

OTHER PUBLICATIONS

J. Lewandowski, et al., An attempt to Improve Selectivity of the Amperometric . . . , vol. 5, (Suppl.) pp. 749–752.

J. Lewandowski, et al., Electrocatalytic Determination of Glucose in a Ringer's Solution . . . , Feb. 1986, pp. 147–152.

S. P. Bessman, et al., The Implantation of a Closed Loop Artificial Beta Cell in Dogs, vol. XXVII (1981), pp. 7–18.

J. Lewandowski, et al., In Situ Generation of Active Catalytic Layer on Glucose Sensing . . . , vol. XXXI (1985), pp. 434–438.

Jan J. Lewandowski, et al., "Electrocatalytic Determination of Glucose with Pulse-Polarography," 1985, pp. 2–11 & Tables.

L. D. Burke, et al., "Hydrous Oxide Formation On Platinum–A Useful Route to Controlled Platinization," pp. 315–334, 1984.

J. J. Lewandowski, et al., "System for Extracorporeal Glycemia Monitoring with an Amperometric Glucose Sensor," 1983, pp. 439–444.

H. Harasaki et al., "Cross-Linked Gelatin As A Blood Contacting Surface," 1979, pp. 216–221.

*Primary Examiner*—John F. Niebling
*Assistant Examiner*—Ben C. Hsing
*Attorney, Agent, or Firm*—Fay, Sharpe, Beall, Fagan, Minnich & McKee

[57] ABSTRACT

A glucose sensing apparatus and method includes an electrocatalytic sensor having a reference electrode and a sensing electrode. A periodic signal is comprised of a ramp voltage which is intermingled a series of square wave measurement pulses. This signal is applied to the sensor. Current levels are sampled twice during each measurement pulse, and a signal indicative of glucose level is derived therefrom. After completion of a measurement, a reactivation, signal is applied to the electrode to regenerate deteriorated surfaces thereof.

22 Claims, 7 Drawing Sheets

PULSE VOLTAMMETRY

BACKGROUND OF THE INVENTION

This application is a continuation-in-part of Application Ser. No. 930,872, filed Nov. 14, 1986, now abandoned which in turn is a continuation-in-part of Application Ser. No. 815,402, filed Dec. 31, 1985, now abandoned.

The present application pertains to the art of monitoring physiological characteristics, and more particularly to sensing of glucose concentrations in biological fluids.

It is often desirable to accurately monitor a content of glucose in biological fluids, particularly, a glucose level of blood. Accurate data representing a glucose level provides a valuable tool for patient care, such as for providing accurate timing of insulin injections in diabetic patients.

Techniques for monitoring glucose levels include both enzymatic and electrocatalytic methods. In enzymatic sensors, glucose is oxidized with the aid of a glucose oxidase into gluconic acid, such that oxygen is consumed and hydrogen peroxide is formed. The consumption of oxygen, as well as the formation of hydrogen peroxide, is electrochemically measured. A signal related to the concentration of glucose is thus obtained.

Problems are frequently encountered while using the electrocatalytic measurement method. Such problems are often attributed to the presence of secondary fluid constituents, such as amino acids and urea, in those fluids in which glucose measurement is desired.

An earlier attempt to minimize the effect of these interfering substances was disclosed in U.S. Pat. No. 4,340,458 to Lerner, et al. This system impressed a sensor with a trapezoidal waveshape, and implemented integration techniques during the rise and fall periods thereof to separate glucose related signals from interfering ones. During the constant voltage periods of the trapezoidal waveshape of Lerner et al., deposits are "burned off" to aid in decreasing degradation of the sensor. While this presented an improvement, the electrodes still degraded more rapidly than is generally desirable. Additionally, complex circuitry is required to implement the system.

Additional problems, such as poisoning, may result from the use of electrocatalytic methods. Such poisoning occurs with high catalytic working electrodes, such as those which are implemented for their wide concentration range for detection. Low catalytic load working electrodes, while less susceptible to poisoning, and with longer term stability, are often not used due to their narrow glucose concentration detection range. It is desirable therefore to have a means by which a low catalytic working electrode, with its corresponding long term stability, could be made workable.

The alternative, enzymatic method has become popular due to its high selectivity to glucose. Several working systems embodying this technology are commercially available. A problem with enzymatic sensors is experienced, however, with prolonged, continuous exposure to body fluids, especially when such exposures are in excess of 72 hours. When exposed for such durations, the enzymatic sensors exhibit significant and irreversible loss of sensitivity to glucose.

Additional problems result from deposits from blood constituents on membranes which line sensors, due in part to lack of biocompatibility.

The present invention contemplates a new and improved system which solves the above problems, and others, and provides an electrocatalytic sensor with improved accuracy, adapted for relatively long term use in a test specimen.

SUMMARY OF THE INVENTION

In accordance with the present invention, there is provided an apparatus for sensing chemical compositions. An electrocatalytic sensor, having at least a sensing electrode and a reference electrode, has a periodic signal applied thereto during a measurement time period. Means is provided for applying a periodic reactivation signal to the sensor during a reactivation time period. Sensing means is provided for sensing electrical conduction between the electrodes during the measurement time period.

In accordance with a more limited aspect of the present invention, a second periodic signal is applied to the sensor during the measurement time period. The second periodic signal is defined by an amplitude and frequency less than that of the first periodic signal.

In accordance with a still more limited aspect of the present invention, the second periodic signal is generated as a plurality of generally square wave pulses.

In accordance with a still more limited aspect of the present invention, first and second measured values are obtained from the sensing means during each of the plurality of the measurement pulses, and a signal indicative of a chemical level is derived therefrom.

In accordance with another aspect of the present invention, a method is provided for sensing chemical compositions which includes providing a first periodic signal to an electrocatalytic sensor during a measurement time period. A reactivation signal is applied to the sensor during a reactivation time period. The reactivation signal differs from the first periodic signal by at least one of amplitude, frequency, and waveshape. A second periodic signal is applied to the sensor during the measurement time period. The second periodic signal has a lower amplitude and a higher frequency less than an amplitude and frequency of the first periodic signal. Electrical conduction between the first and second electrodes of the sensor is sensed during the measurement time period.

An advantage of the present invention is the provision of a simple and accurate chemical sensing device.

Another advantage of the present invention is the provision of a glucose sensor with an increased effectiveness during prolonged exposure to biological fluids.

Yet another advantage of the present invention is the provision of a biocompatible glucose sensor.

BRIEF DESCRIPTION OF THE DRAWINGS

The invention may take physical form in certain parts and arrangements of parts, preferred and alternate embodiments of which will be described in detail in the specification and illustrated in the accompanying drawings which form a part hereof and wherein.

DETAILED DESCRIPTION OF THE PREFERRED AND ALTERNATE EMBODIMENTS

Figure 1:
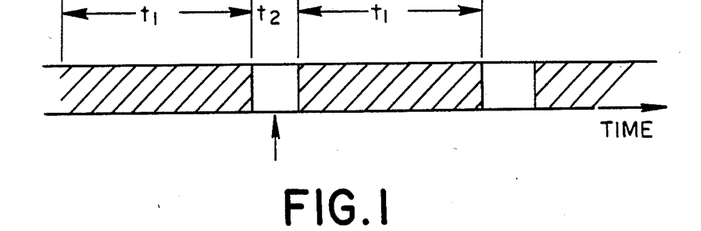
FIG. 1 is a graph illustrating a progression of measurement and reactivation time periods in accordance with voltages applied to a sensor of the present invention.

Referring now to the drawings where the showings are for the purposes of illustrating the preferred embodiment of the invention only and not for the purpose of limiting the same, FIG. 1 illustrates a cyclic measurement and reactivation schedule as implemented in accordance with the present system.

Figure 2:
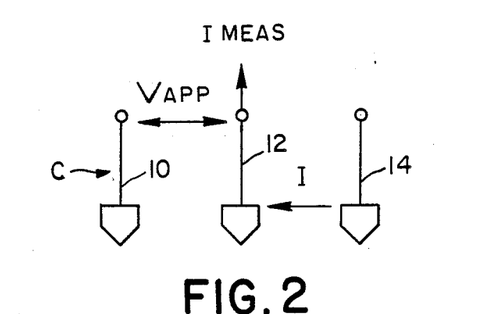
FIG. 2 diagrammatically illustrates a suitable sensor for use with the present invention.

A suitable sensor, such as the three electrode sensor which is diagrammatically illustrated in FIG. 2, is intermittently subjected to a series of measurement periods, such as that illustrated at A, and reactivation or regeneration periods, such as that illustrated at B. In the preferred embodiment, each measurement period is of generally uniform duration $t_1$ and each reactivation period B has a generally uniform duration $t_2$. This cyclic measurement and reactivation scheme provides for increased accuracy and longevity of measurements taken from electrodes in conjunction with the present invention. As illustrated by FIG. 1, the measurement period A is preferably greater than the reactivation period B. The magnitude of the particular durations will be disclosed in more detail below.

Turning now to FIG. 2, a suitable sensor is illustrated. The sensor C is illustrated as a three electrode sensor. Included is a reference electrode 10, a sensing or working electrode 12, and a counter electrode 14. Suitable three electrode devices are well known in the art, and attention is drawn to U.S. Pat. No. 4,340,458, which is incorporated herein by reference, in which a suitable three electrode sensor has been provided for use in a glucose sensor. It will be appreciated, however, that suitable two electrode sensors, as are well known in the art, may be implemented. Such a two electrode structure is formed by combining functions of the reference electrode and the counter electrode 14 in a single electrode. The increased accuracy and performance of three electrode sensors is, however, generally desirable.

In the present invention, voltage signals are applied at varying levels between the reference electrode 10 and the sensing electrode 12. When the sensor is exposed to substances with suitably measurable chemical properties, such as glucose, such an applied voltage induces a current flow I between the counter electrode 14 and the sensing electrode 12, as is illustrated in FIG. 2. Properties of the applied voltage level signal will be more fully illustrated below.

Induced current between the counter electrode 14 and the sensing electrode 12 may be measured by conventional means for selectively monitoring current and generating a signal representative of the magnitude thereof.

Figure 15:
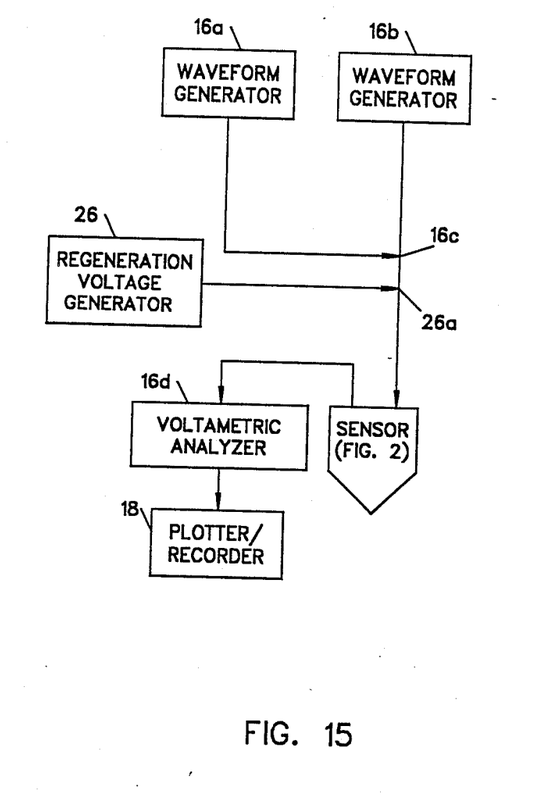
FIG. 15 illustrates, in block diagram form, the waveform generation/analyzer circuitry of the subject invention.

Turning briefly to FIG. 15, a suitable device for monitoring and providing a waveform during measurement illustrated. An IBM EC 225 Voltametric Analyzer (Danbury, Conn.) suitably forms waveform generators 16a and 16b, a means for commingling outputs therefrom 16c, and a voltametric analyzer 16d. A signal generated by the analyzer 16c is suitably plotted and compared by a plotter/recorder 18 suitably comprised by an 815 M Plottomatic XY Recorder (Salem, N.H.).

Figure 3:
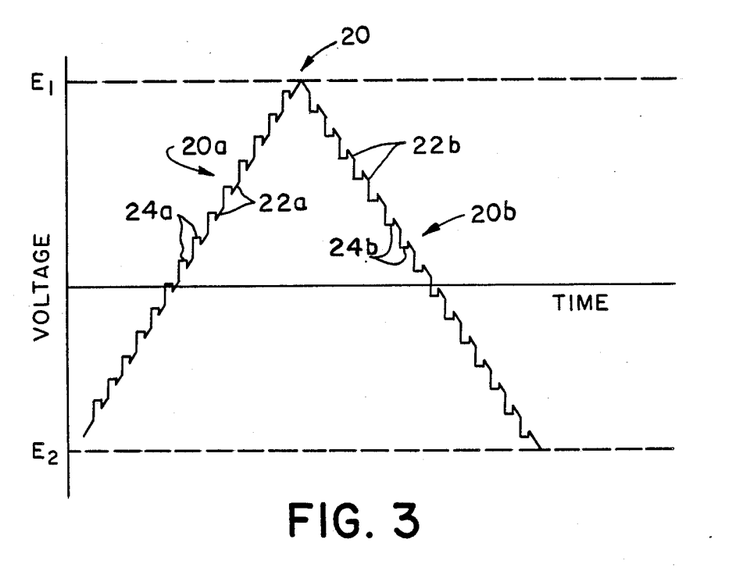
FIG. 3 is a voltage versus time graph illustrating a signal suitably applied to the sensor of FIG. 2 during the measurement time period of FIG. 1.

Turning now to FIGS. 3 through 5, the particular waveforms implemented in the measurement period A and reactivation B of FIG. 1 will be described. Turning particularly to FIG. 3, the signal applied to the sensor C during the measurement period A is illustrated. A composite measurement signal 20, illustrated with a rising voltage level portion 20a and a falling voltage level portion 20b, is formed by a commingling of a first periodic signal 22 and a second periodic signal 24. As illustrated, the first periodic signal 22 is defined by a generally a triangular waveshape, and is illustrated with a generally increasing voltage portion 22a and a generally decreasing voltage portion 22b. The second periodic signal 24 is illustrated with a generally increasing voltage level portion 24a and a generally decreasing voltage level portion 24b. During the measurement or analytical phase A (FIG. 1), the sensing or working electrode 12 is continuously polarized with the first periodic signal 22 which, as illustrated, is comprised of a triangular carrier waveform.

As noted above, prior enzymatic methods of glucose sensing avoided use of platinum electrodes due to their poor selectivity to glucose. The platinum electrode is, however, preferable due to its increased stability to interaction with body fluids during in vivo usage. The pulse voltammetry technique of the subject system provides sufficient sensitivity to facilitate use of such platinum electrodes. It is therefore preferable to have both the counter electrode 10 and the sensing electrode 12 comprised of platinum, and the reference electrode comprised of silver. Stability of and reproductability of the electrocatalytic sensor is related to the stability of its inorganic catalytic surface (platinum black) of its platinum working electrode.

The catalytic activity of the platinum electrode lessens or degrades during the course of operation by blockage of active sites caused by adsorption of by-products of reactants and organic compounds, and by a decrease in a number of active sites due to structural changes of the catalytic surface.

During the analytical or measurement period, the working electrode is continuously polarized with the first periodic signal 22. The first periodic signal 22, as illustrated, has a maximum voltage or upper limit ($E_1$) and a minimum voltage or lower limit ($E_2$). Acceptable decontamination is presented when the upper limit $E_1$ is in the range of 0.8 volt to 2.5 volts and the lower limit $E_2$ is in the range of $-0.7$ volt to $-1.5$ volts. A suitable wave also has a voltage change in relation to time (the slope of the first periodic signal wave 22) in the range of $+/-50$ to $+/-200$ m v/sec; the sign being dependent on whether the voltage is rising or falling. Optimal results are obtained with an upper limit $E_1$ generally at 1.0 volt and a lower limit $E_2$ generally at $-1.0$ volt. With these ranges, it will be seen that a duration of one leg of the composite measurement signal, that is, a time duration between the maximum voltage $E_1$ and the minimum voltage of $E_2$ extends in the range of 10 seconds to forty seconds. A full cycle therefore, that is to say, $E_2$ to $E_1$ to $E_2$, therefore extends in the range of 20 seconds to 80 seconds minutes.

Variations of the upper limit and lower limit allow for modification and optimization of decontamination parameters associated with a sensor in order to obtain higher catalytic activity, better stability, and better control of background current.

Figure 4:
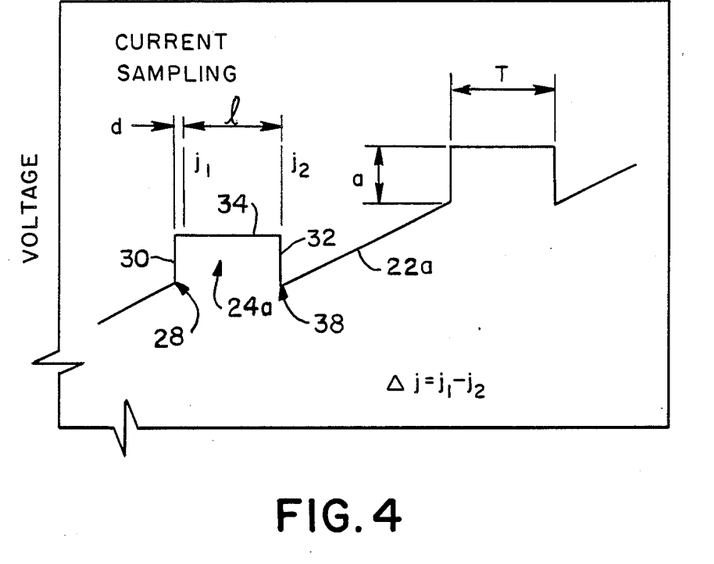
FIG. 4 is an enlargement of a portion of the curve of FIG. 3.

With additional reference to FIG. 4, the parameters of a suitable second periodic signal 24, which is commingled with the first periodic signal 22, will be described. For ease in illustration, discussion is made only with reference to the rising voltage portions 22a, 24a. It will be understood, however, that similar properties are had with respect to the falling voltage portions 22b, 24b, except as will be particularly noted below.

As illustrated, the second periodic signal 24 is preferably comprised of a series of pulses defined as having a generally square waveshape. Two such pulses are shown in FIG. 4. In the preferred embodiment, all pulses have generally similar characteristics, and are defined with an amplitude a and a duration T. The pulses of the second periodic signal 24 are commingled with the first periodic signal 22. With the understanding that, in the preferred embodiment, all pulses of the second periodic signal 24 are generally uniform, description will be made with reference to one pulse only.

A progression of the first periodic signal 22 is interrupted or suspended at time or voltage point 28. At this point imposition of the square wave pulse 24a is commenced. In the preferred embodiment, each square wave pulse has an amplitude a in the range of 20 millivolts to 100 millivolts and a duration T in the range of 0.1 second to 0.6 second.

A first current measurement $i_1$ is taken from the sensor C (FIG. 2) after a slight delay d from a leading edge 30 of pulse 24a. A second current measurement $i_2$ is subsequently read from the sensor after a lag time l after the first measurement $i_1$. Preferably, the second measurement $i_2$ is obtained at or near a trailing edge 32 of pulse 24a. Therefore, both current measurements $i_1$ and $i_2$ are taking at a generally uniform voltage level, illustrated by the top portion 34 of pulse 24a, of second periodic signal 24. A chemical level signal $\Delta i$ is derived as a difference between the current $i_1$ and $i_2$. In a glucose sensor, the current difference $\Delta i$ provides a signal indicative of the glucose content of a substance being analyzed, at a voltage range determined by the first waveform.

After completion of the pulse 24a at the trailing edge 32, the first periodic signal 22 is recommenced at recommencement point 38. In the preferred embodiment, the voltage level of the first periodic signal 22 at the recommenced point 38 is generally equal to the voltage of the first periodic signal at the suspension point 28. This is suitably accomplished by temporarily holding progression of the voltage of the first periodic signal 22, or alternatively, by commingling the first and second periodic signal in superposition form. In the latter embodiment, a suitable waveshape for each pulse of the second periodic signal 24 is chosen to allow for superpositioning with the first periodic signal 22 so as to form a composite measurement signal having a top portions of a generally uniform voltage analogous to that top portion of the pulse 24a.

Referring again to FIG. 3, differences of the composite measurement signal 20 as between first and second portions 20a and 20b, present in the preferred embodiment, will be described. The first portion 20a shows a generally increasing voltage from $E_2$ to $E_1$, while the portion 20b shows a generally decreasing voltage from $E_1$ to $E_2$. The overlap of the first periodic signal is, in either instance, implemented to facilitate the formation of the generally uniform voltage level 34 to take at least the two current samplings. As illustrated in the portion 22b, however, each pulse of the second periodic signal 24 results in a lowering of the voltage over that present by the first periodic signal 22, standing alone. After completion of each pulse, the voltage of the leg 22b returns up to the voltage level at which it was suspended.

Figure 5:
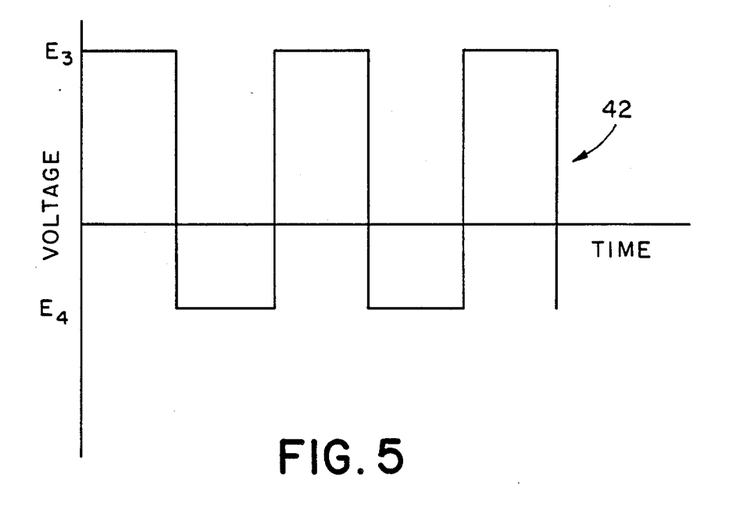
FIG. 5 is a voltage versus time graph of a signal suitably applied to the sensor of FIG. 2 during the reactivation period of FIG. 1.

Turning particularly to FIG. 5, with additional reference to FIG. 1 and FIG. 15, a voltage level which is impressed on a sensor during the reactivation period B will be described. A suitable regeneration voltage generator means 26 (FIG. 15) for generation of a regeneration voltage for application to the glucose sensor is a Heath Schlumberger function generator EU81A (Bentor Harbour, Mich.), which serves to apply the regeneration voltage to the sensor through a means 26a. A periodic reactivation signal 42 preferably has a frequency of oscillation in the range of 20 hertz to one kilohertz. In the preferred embodiment, the reactivation signal 42 is defined by a generally square waveshape. During the reactivation period B, which is suitably a five to twenty minute duration, the platinum sensing electrode 12 is polarized versus the reference electrode 10 with square wave pulses of a generally constant frequency. Optimal results have been found where the upper limit $E_3$ is generally in the range of 1.2 volts to 1.7 volts, and the lower limit $E_4$ is in the range of $-0.2$ volt to $-0.6$ volt. Imposition of this reactivation signal functions to reactivate sensitivity of the sensor.

At anodic polarization (the positive portion of the reactivation signal), a surface platinum oxide and/or hydroxide is formed, and at the same time, is partially dissolved forming palatinate ions. When the reactivation signal 42 is switched towards the cathodic (negative) level, dissolved platinum is reduced and redeposited on the surface of the sensing or working electrode 12. Redeposited platinum creates a renewed surface exhibiting renewed high catalytic properties. The improved characteristics of the noted wave forms on the sensor has been demonstrated experimentally.

Figure 6:
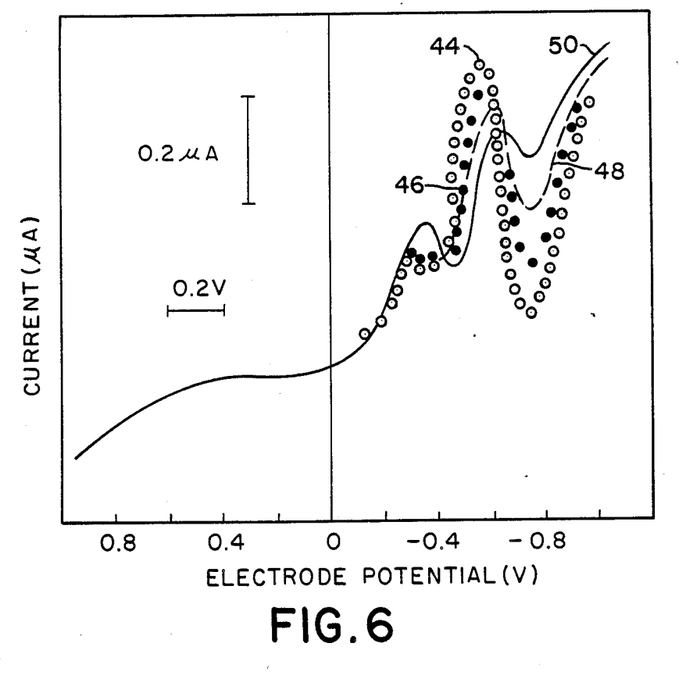
FIG. 6 is a diagram of current measured by an apparatus of the present invention, versus electrode potential (pulse voltamograms) at different glucose concentrations.

Turning to FIG. 6, a graph illustrating a relation of current changes induced by commingling of pulses of the second periodic signal 24 onto the first periodic signal 22 is illustrated. Curves 44, 46, 48, and 50 represent changes and current resultant from varying glucose concentrations and a substance under examination. Cathodic peaks are present at generally the levels of −0.35 volt, −0.5 volt, and −0.75 volt, the voltage being determined by the first waveform. The most pronounced changes are in the −0.75 volt level, and these current levels are therefore most appropriate for forming a glucose related signal on the sensing electrode 12 (FIG. 1).

It will be seen that glucose level signals which are obtained are thereby related to kinetic, rather steady-state processes. In cases where several electrochemical reactions are overlapping, such as those induced by urea and glucose, the particular process can be distinguished by its unique dynamic behavior when current approaches its new steady-state value of perturbation. The dynamic method of measurement with voltammetry permits the use of low catalytic, active, but more stable, platinum electrode with better linearity of its calibration plot compared to prior cyclic voltammetry measurements.

Figure 7:
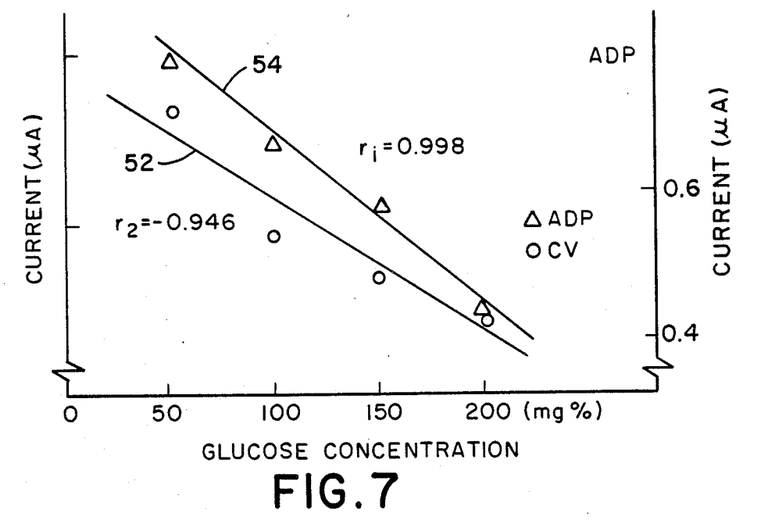
FIG. 7 is a diagram of glucose concentration versus current, measured with the present invention.

The improvements realized by implementation of the system of the present invention are evidenced with reference to FIG. 7. Therein, the curve 52 represents a glucose concentration level obtained by prior, cyclic voltammetry ("CV"), techniques. The curve 54 illustrates those results acquired by the pulse voltammetry system of the present invention. It will be seen that a correlation coefficient $r_1$ of the present system more nearly approaches a desired one-to-one relationship than that regression coefficient $r_2$ of the curve 52 obtained from prior techniques.

Figure 8:
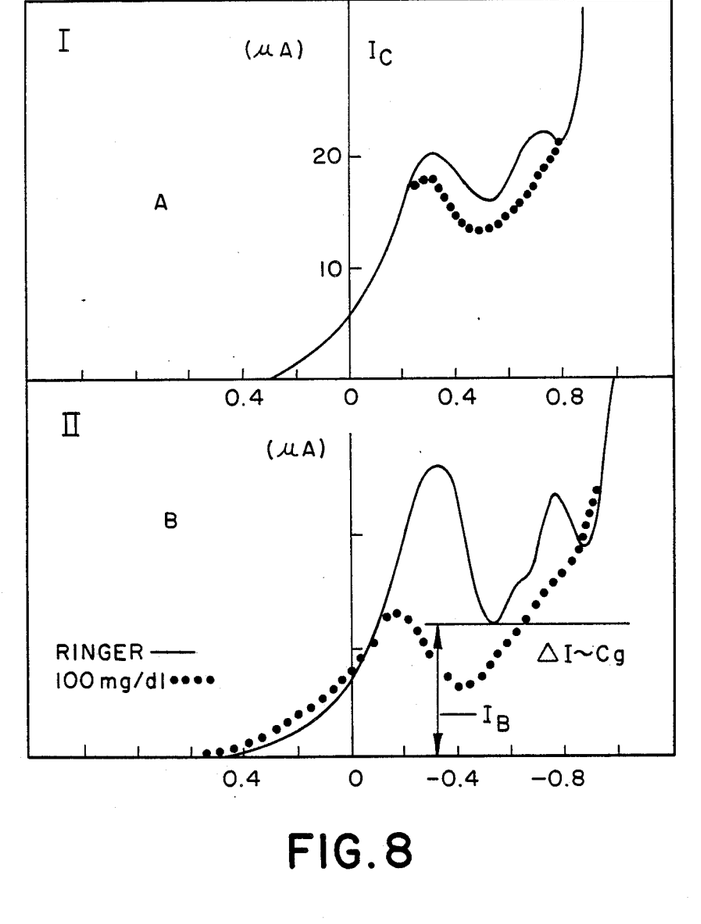
FIG. 8 is a diagram of measured current versus applied voltage before and after cyclic activation of a sensor in conjunction with the present invention.

Turning to FIG. 8, a graph exemplifying the effect of the above-disclosed, fast-cycling, activation of catalytic activity on a smooth platinum electrode is presented. Depicted therein is a plot of a cathodic scan of a platinum electrode in Ringer's solution (scan speed equals 100 mV/sec.) Section I of FIG. 8 depicts measured values prior to activation, while Section II depicts measured valves thereafter. The plots section II of FIG. 8 were obtained for a platinum smooth electrode in Ringer's solution (solid line) and a Ringer's solution containing glucose of a concentration of 100 mG/dl (dotted line). The activation was applied in the range of $E_3$ (the upper limit of FIG. 3) equals 2.0 volts to $E_1$ (the lower limit of FIG. 5) equals −0.5 volt (versus colomel reference electrode), at a frequency of 200 hertz for five minutes. After activation, the electrode was used in the analytical cycle at a scan speed of 100 mV/sec, and an amplitude of +/−1.1 volts (versus colomel).

After 20 minutes of such cycling, cathodic scans were recorded again (FIG. 8 II) for Ringer's (solid line) and glucose solution of concentration 100 mg/dl (dotted line).

With activation of the platinum smooth electrodes, an increase of sensitivity parameters is observed from 18 percent to 40 percent and an increase of background current is noted. In three days of continuous electrode operation with high frequency activation, the sensitivity decrease was five percent while the background current increase was 20 percent of its initial value. Without activation, a decrease of background current to 40 percent of the initial value after the first 24 hours, and sensitivity decreases to 50 percent of initial value was observed. The glucose contents, $C_g$, is a function of the current change $\Delta I$.

Turning now to FIGS. 9 through 13c, various sensors which are suitable for implementation in the present invention are disclosed. It will be noted that in each, three electrodes are present. The three-electrode system is necessary for increased accuracy of the instant glucose sensor. While, as noted above, a two-electrode structure may be implemented by combining the reference electrode and the counter electrode functions in a single electrode.

Figure 9:
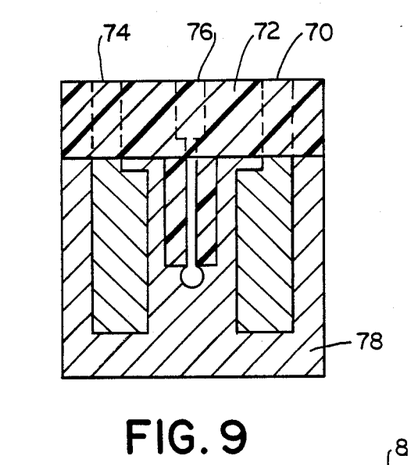
FIG. 9 is a top view through a central portion of a semi-permeable membrane of one embodiment of a subcutaneous sensor, having the substrate illustrated in an elevational view, with selected portions of its electrodes shown in phantom.

FIG. 9 depicts a sensor, suitable for subcutaneous use, with a single anode sensing electrode. The reference electrode 70 is deposited on an insulating substrate 72 to counter electrodes 74 and a sensing or working electrode 76. A semi-permeable membrane 78, the properties of which will be described further below, is deposited directly on the electrodes.

Figure 10:
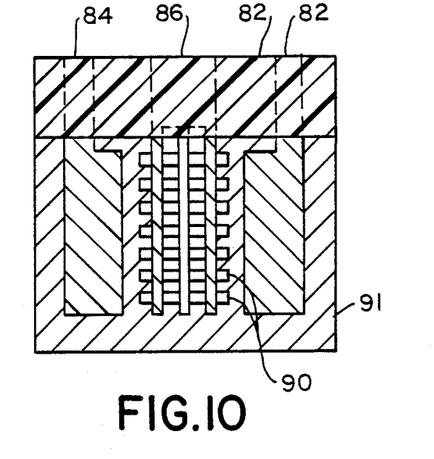
FIG. 10 is an alternate embodiment to the sensor of FIG. 9, depicted in similar fashion thereto.

FIG. 10 depicts a similar, subcutaneous type, sensor suitable for implantation. A reference electrode 80 is deposited on an insulating substrate 82 to a counter electrode 84 and a sensing electrode 86. A semi-permeable membrane 88, similar to that of FIG. 9, is shown deposited about the electrodes. The sensing electrode 86 is, in this instance, a multi-anode version comprised of a plurality of thin plates 90. Again, a semi-permeable membrane 91 is deposited about the electrons.

Figure 11:
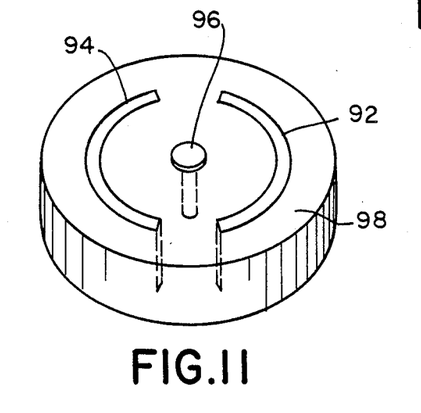
FIG. 11 is one embodiment of a catheter-type sensor.

FIG. 11 depicts a catheter-type sensor. Therein, reference electrode 92 is interconnected with counter electrode 94 and sensing electrode 96 by a semi-permeable membrane 98.

Figure 12A:
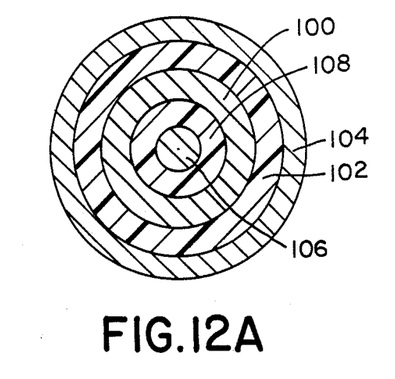
FIG. 12A is a front view of an alternate embodiment of the catheter-type sensor of FIG. 11.
Figure 12B:
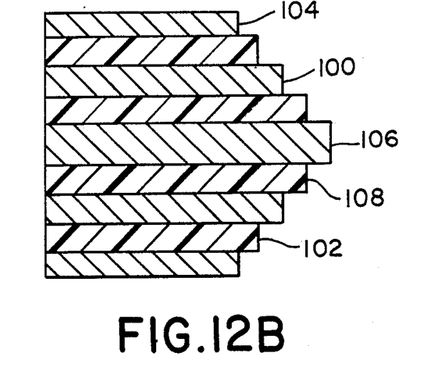
FIG. 12B is a side view of the sensor of FIG. 12A.

An alternate embodiment of a catheter-type sensor is depicted in FIGS. 12A and 12B. Therein, a plurality of concentric cylindrical components are implemented in the sensor. A reference electrode 100 is separated by insulator 102 from counter electrode 104. Sensing electrode 106 is separated from counter electrode 100 by insulator 108.

Figures 13A, 13B, 13C:
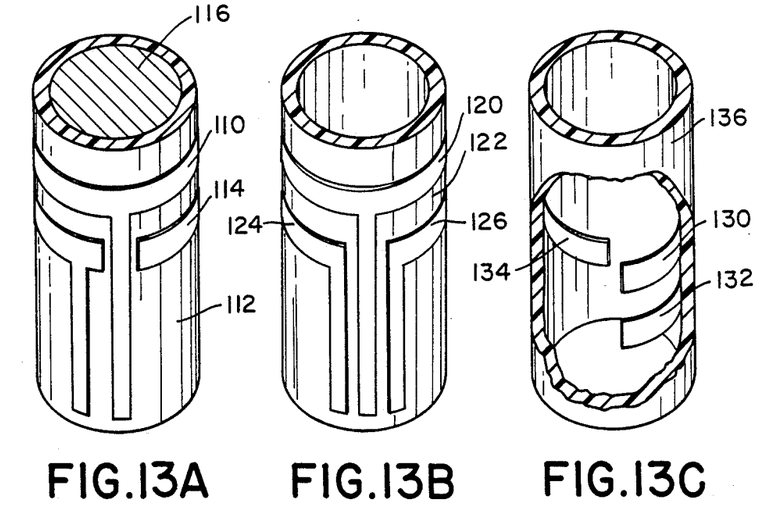
FIG. 13A is one embodiment of a tube-type sensor.
FIG. 13B is an alternate embodiment of the tube-type sensor of FIG. 13A.
FIG. 13C is an alternate embodiment of the tube-type sensors of FIGS. 13A and 13B.

FIGS. 13A through 13C depict tube-type sensors. In FIG. 13A, the reference electrode 110 is separated by insulating substrate 112 from counter electrode 114 and sensing electrode 116. FIGS. 13B and 13C depict hollow tube-like sensors. In FIG. 13B, the reference electrode 120 is mounted on an exterior of insulator 122. The sensing electrode 124 and the counter electrode 126 are similarly mounted on the insulator 122. In FIG. 13C, a reference electrode 130 is mounted on an interior of insulator 132. The sensing electrode 132 and the counter electrode 134 are similarly mounted on the interior of insulator 136. The embodiment of FIG. 13C is therefore adapted for a flow-through sensor application.

Figure 14:
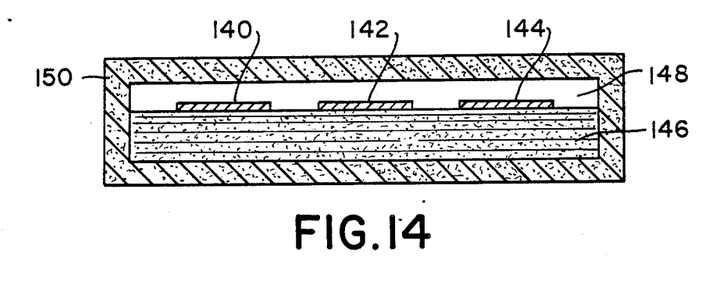
FIG. 14 illustrates a sensor which has been coated with a biolyzing substance.

Turning to FIG. 14, a desirable coating material to be placed on electrodes placed in contact with bodily fluids will be described. It is desirable to have a biocompatible coating membrane on the exterior of the electrodes to facilitate operation in vivo (secondary membrane). This is especially desirable for the working or sensing electrode. A semi-permeable membrane (primary membrane) separating the electrodes from the solution into which a sensor is placed is desirable deposited directly on the electrodes. A sensor is typically fabricated from non-biocompatible materials. A dialyzing membrane protects the electrode from high molecular blood and body fluid components (primary membrane).

To avoid blood cell deposition on the surface and avoid blood clotting, the sensor is biolized or coated with a cross-linked gelatin (secondary membrane) with good biocompatiblity. Suitable membranes for coating have a nominal height cut-off of less than 10,000 daltons. Suitable, commercially available, (primary) dialyzing or reverse osmotic membranes include: Cuprophan dialyzing membrane, Emka Wuppertal, West Germany; Diaflo Ultrafiltration Membranes, Amicon Corp., Lexington, Mass.; and Pellican Membranes, Millipore Corp., Bedford, Mass.

With particular reference to FIG. 14, electrodes 140, 142 and 144 are exemplarily illustrated to be mounted on substrate 146. Surrounding the electrodes 140, 142, 144 is a dialyzing (primary) membrane 148. Finally, the structure is entirely encased in the biolyzed layer 150 to render it biocompatible (secondary). At least the working platinum electrode, and preferably, all electrodes are therefore, screened with a semi-permeable dialyzing membrane and biolyzation procedure (coating total structure with a biocompatible gelatin, cross-linked layer).

The dialyzing membrane 148 screens the electrode against poisoning from a high-molecular weight components. A lack of such a membrane renders it extremely difficult to accurately measure glucose in blood, plasma, or other bodily fluids with an electrocatalytic sensor. As all components of the sensor are fabricated from generally nonbiocompatible materials, it is further desirable to accomplish biolyzation of the total structure to avoid blood cell deposition on a cloth formalization on the sensor. This is achieved by coating the sensor with the biolyzed layer 150 of the cross-linked gelatin.

The invention has been described with reference with preferred and alternate embodiments. Obviously, modifications and alterations will occur to others upon the reading and understanding of the specification. It is our intention to include all such modifications and alterations insofar as they come within the scope of the appended claims or the equivalents thereof.

Having thus described our invention, we now claim:

1. A sensing apparatus for sensing chemical compositions comprising:
   an electrocatalytic sensor having at least sensing and reference electrodes;
   means for applying a first periodic signal to the sensor during a measurement time period;
   means for generating a periodic reactivation signal differing from the first periodic signal by at least one of amplitude, frequency, and waveshape;
   means for applying the periodic reactivation signal to the sensor during a reactivation time period after completion of the measurement time period; and
   sensing means for sensing electrical current flow between the sensing and reference electrodes during the measurement time period.

2. The sensing apparatus of claim 1 further comprising means for generating a plurality reactivation pulses defined by a generally square waveshape, which reactivation pulses form the reactivation signal.

3. The sensing apparatus of claim 2 further comprising:
   means for generating a plurality of measurement pulses defined by a generally square waveshape, which measurement pulses form the second periodic signal;
   means for commingling the measurement pulses with the first periodic signal to form a composite measurement signal;
   means for obtaining first and second measured value signals from the sensing means during each of the plurality of measurement pulses; and
   means for deriving a signal indicative of a chemical level in accordance with the first and second measured value signals.

4. The sensing apparatus of claim 1 wherein:
   the reactivation signal has a frequency in the range of 20 hertz to 1 kilohertz;
   and wherein the first periodic signal has a voltage versus time relation in the range of 50 millivolts per second to 200 millivolts per second, in a voltage range of −1.0 volt to 1.0 volt.

5. The sensing apparatus of claim 4 further comprising:
   pulse means for generating a plurality of measurement pulses with a wavelength in the range of 0.1 second to 0.6 second; and
   means for commingling the measurement pulses with the first periodic signal to form a composite measurement signal.

6. The sensing apparatus of claim 5 further comprising:
   means for obtaining first and second measured values from the sensing means during each of the plurality of measurement pulses; and
   means for deriving a signal indicative of a chemical level in accordance with the first and second measured values.

7. A sensing apparatus for sensing chemical compositions comprising:
   an electrocatalytic sensor having at least sensing and reference electrodes;
   means for applying a first periodic signal to the sensor during a measurement time period;
   means for applying a periodic reactivation signal to the sensor during a reactivation time period, the reactivation signal differing from the first periodic signal by at least one of amplitude, frequency, and waveshape; and
   sensing means for sensing electrical current flow between the sensing and reference electrodes during the measurement time period; and
   means for applying a second period signal to the sensor during the measurement time period, the second periodic signal being defined by a lower amplitude and higher frequency than an amplitude and frequency of the first periodic signal.

8. The sensing apparatus of claim 7 further comprising a pulse generating means for generating a plurality of measurement pulses which form the second periodic signal.

9. The sensing apparatus of claim 3 further comprising means for commingling the first and second periodic signals to form a composite measurement signal.

10. The sensing apparatus of claim 9 wherein the pulse generating means further includes means for generating the measurement pulses such that they are defined by a generally square waveshape.

11. The sensing apparatus of claim 10 further comprising:
   means for obtaining first and second measured value signals from the sensing means during each of the plurality of measurement pulses; and
   derivation means for deriving a chemical level signal in accordance with the first and second measured value signals.

12. The sensing apparatus of claim 11 wherein the derivation means includes means for calculating the chemical level signal from a difference between the first and second measured values.

13. A glucose level sensing apparatus comprising:
means for applying a first periodic signal to a sensor during a measurement time period, the first periodic signal being defined with a voltage versus time relation in the range of 50 millivolts per second to 200 millivolts per second, in a voltage range of −1.0 volt to 1.0 volt;
means for applying a periodic reactivation signal to the sensor during a reactivation time period, the reactivation signal having a frequency in the range of 20 hertz to 1 kilohertz;
sensing means for sensing electrical conduction between a sensing electrode and a reference electrode of the sensor during the measurement time period;
means for applying a plurality of measurement pulses defined by a generally square waveshape to the sensor during the movement time period, the measurement pulses being further defined by a lower amplitude and a higher frequency than an amplitude and frequency of the first periodic signal;
means for commingling the first periodic reactivation signal and the plurality of measurement pulses to form a composite measurement signal;
means for obtaining first and second measured value signals from the sensing means during each of the plurality of measurement pulses; and
derivation means for deriving a chemical level signal in accordance with the first and second measured value signals.

14. The sensing apparatus of claim 13 wherein the sensor is encapsulated with a biocompatible coating.

15. A method of sensing chemical compositions comprising the steps of:
applying a first periodic signal, during a measurement time period, to an electrocatalytic sensor having at least sensing and reference electrodes;
applying a periodic reactivation signal to the sensor during a reactivation time period, the reactivation signal differing from the first periodic signal by at least one of amplitude, frequency, and waveshape;
applying a second periodic signal to the sensor during the measurement time period, the second periodic signal having a lower amplitude and a higher frequency than an amplitude and frequency of the first periodic signal; and
sensing electrical current flow between the sensing and reference electrodes during the measurement time period.

16. The method of claim 15 further comprising the step of generating a plurality of measurement pulses which form the second periodic signal.

17. The method of claim 16 further comprising the step of commingling the first and second periodic signals to form a composite measurement signal.

18. The method of claim 17 further comprising the step of generating the measurement pulses such that they are defined by a generally square waveshape.

19. The method of claim 17 further comprising the steps of:
obtaining first and second measured values of sensed electrical current between the sensing and reference electrodes during each of the plurality of measurement pulses; and
deriving a chemical level signal in accordance with the first and second measured values.

20. The method of claim 19 wherein further comprising the steps of calculating the chemical level signal as a difference between the first and second measured values.

21. The method of claim 15 further comprising the steps of generating a plurality reactivation pulses defined by a generally square waveshape, which reactivation pulses form the reactivation signal.

22. The method of claim 21 further comprising the steps of:
generating a plurality of measurement pulses defined by a generally square waveshape;
commingling the measurement pulses with the first periodic signal to form a composite measurement signal;
obtaining first and second measured values during each of the plurality of measurement pulses; and
deriving a signal indicative of a chemical level in accordance with the first the first and second measured values.

* * * * *